United States Patent
Horsup

(10) Patent No.: US 7,628,060 B2
(45) Date of Patent: Dec. 8, 2009

(54) DEPOSIT REMOVAL PROBE AND METHOD OF USE

(75) Inventor: David I. Horsup, Bellaire, TX (US)

(73) Assignee: Nalco Company, Naperville, IL (US)

( * ) Notice: Subject to any disclaimer, the term of this patent is extended or adjusted under 35 U.S.C. 154(b) by 138 days.

(21) Appl. No.: 11/608,065

(22) Filed: Dec. 7, 2006

(65) Prior Publication Data

US 2008/0134770 A1      Jun. 12, 2008

(51) Int. Cl.
*G01N 17/00* (2006.01)
(52) U.S. Cl. .............................................. 73/86; 422/53
(58) Field of Classification Search ..................... 73/86; 166/902; 422/53
See application file for complete search history.

(56) References Cited

U.S. PATENT DOCUMENTS

| | | | | |
|---|---|---|---|---|
| 1,608,869 A | * | 11/1926 | Tilton | 166/300 |
| 2,433,718 A | * | 12/1947 | Teplitz | 250/260 |
| 2,664,744 A | * | 1/1954 | Bilhartz et al. | 422/53 |
| 3,174,332 A | * | 3/1965 | Echtler, Jr. et al. | 73/86 |
| 4,603,113 A | * | 7/1986 | Bauer | 436/6 |
| 4,688,638 A | * | 8/1987 | Williams | 166/250.11 |
| 4,928,760 A | * | 5/1990 | Freitas | 166/113 |
| 5,010,776 A | * | 4/1991 | Lucero et al. | 73/863.23 |
| 5,059,790 A | * | 10/1991 | Klainer et al. | 250/227.21 |
| 5,095,977 A | * | 3/1992 | Ford | 166/113 |
| 5,996,423 A | * | 12/1999 | Baghel et al. | 73/863.23 |
| 6,106,779 A | * | 8/2000 | Buechler et al. | 422/55 |
| 6,131,443 A | * | 10/2000 | Duncan | 73/86 |
| 6,196,074 B1 | * | 3/2001 | Varhol | 73/863.23 |
| 6,272,938 B1 | * | 8/2001 | Baghel et al. | 73/863.23 |
| 7,318,910 B2 | * | 1/2008 | Kin et al. | 422/88 |

OTHER PUBLICATIONS

International Search Report for PCT/US2007/08654.
Written Opinion PCT/US2007/08654.

* cited by examiner

*Primary Examiner*—John Fitzgerald
(74) *Attorney, Agent, or Firm*—Edward O. Yonter; Michael B. Martin

(57) ABSTRACT

A deposit removal probe for monitoring the effectiveness of a chemical at removing deposits from the internal surface of a pipeline used to transport fluids comprising a chamber constructed from mesh having a pore size sufficient to retain a sample of said deposit in said chamber while also allowing the deposit to be removed from the chamber with the action of the chemical and liquid flow through the pipeline and methods of using the probe to determine the effectiveness of a chemical at removing deposits from the internal surface of a pipeline and monitor corrosion rates of surfaces in contact with the deposit and in the bulk fluid.

19 Claims, 1 Drawing Sheet

DEPOSIT REMOVAL PROBE AND METHOD OF USE

TECHNICAL FIELD

This invention relates to monitoring corrosion and deposits in pipelines used to transport fluids. More particularly, this invention concerns a novel deposit removal probe and its use for monitoring corrosion rates and the effectiveness of chemical treatments for removing deposits from pipelines.

BACKGROUND OF THE INVENTION

During the production of crude oil and gas, deposits can be laid down onto the surface of the pipes through which the crude oil, gas, water or a combination thereof is transported. These deposits may be organic (paraffin, asphaltenic), inorganic (scales such as calcium carbonate, barium sulfate, iron sulfide etc.), mineral (sand, clay etc.) or microbial (bacterial material) in nature. The deposits can accumulate on the surface of the pipe and provide a physical barrier that prevents corrosion inhibitor chemicals from penetrating and protecting the surface of the metal. Additionally, concentration cells can be set up between areas of the pipe that are covered with debris and those that are exposed. This can lead to high localized corrosion rates. Additionally the deposits can provide a safe haven for bacteria to grow. Biocidal chemicals can be ineffective at penetrating these deposits. The metabolic by-products of these bacteria can be very acidic and cause localized corrosion.

In the industry today there are few effective methods for measuring the accumulation of deposits on a pipe surface or the effectiveness of chemical programs for removing these solids. Pipeline inspection methods such as ultrasound and radiography can give a qualitative indication of the amount of debris in a pipe. These techniques are time consuming, expensive and require specialized equipment and trained personnel to perform the measurements.

SUMMARY OF THE INVENTION

This invention is a novel deposit removal probe which provides an easy, inexpensive way of quantifying the deposit removal efficiency of chemical treatments.

In an embodiment, this invention is a deposit removal probe for monitoring the effectiveness of a chemical at removing deposits from the internal surface of a pipeline used to transport fluids comprising a chamber constructed from mesh having a pore size sufficient to retain a sample of said deposit in said chamber while also allowing the deposit to be removed from the chamber through the mesh with the action of the chemical and liquid flow through the pipeline.

In another embodiment, this invention is a method of monitoring the effectiveness of a chemical at removing deposits from the internal surface of a pipeline comprising a) providing a probe comprising a chamber constructed from mesh having a pore size sufficient to retain a sample of said deposit in said chamber while also allowing the deposit to be removed from the chamber through the mesh with the action of the chemical and liquid flow through the pipeline; b) placing a weighed sample of said deposit in said chamber; c) inserting said probe in said pipeline; d) adding a known amount of said chemical to said fluids being transported in said pipeline; e) periodically removing said probe from said pipeline and weighing said deposit sample; and f) determining the amount of said sample dissolved or dispersed by said chemical.

In another embodiment, this invention is a method of determining the corrosion rate of an internal surface of a pipeline used to transport fluids wherein said surface is in contact with deposits in said pipeline comprising a) providing a probe comprising a chamber constructed from mesh having a pore size sufficient to retain a sample of said deposit in said chamber while also allowing the deposit to be removed from the chamber with the action of the chemical and liquid flow through the pipeline; b) placing a weighed corrosion coupon having the saine metallurgy as said pipeline in said chamber; c) placing a weighed sample of said deposit in said chamber such that said corrosion coupon is in contact with said deposit sample; d) inserting said probe in said pipeline; e) periodically removing said probe from said pipeline and cleaning and weighing said corrosion coupon; and D determining the corrosion rate of said metallurgy in contact with said deposit.

DETAILED DESCRIPTION OF THE INVENTION

Figure 1:
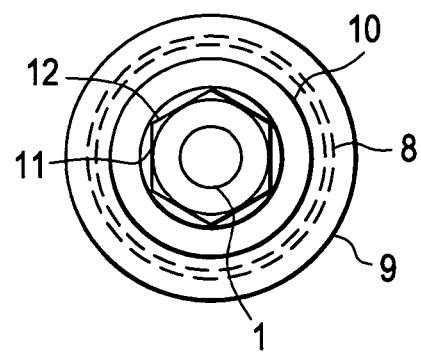
FIG. 1 is a top view of a deposit removal probe according to an embodiment of this invention.

The Deposit Removal Probe (DRP) of this invention is designed to be inserted into a pipeline through which a bulk liquid is flowing in order to evaluate the effectiveness of chemical treatments at removing deposits from the surface of pipelines and/or determine the rate of corrosion under deposits and in the bulk fluid.

The DRP should be constructed of materials which axe inert to the liquid in which the probe is immersed and have enough rigidity to withstand the stress placed on it by the liquid flow over the probe. The shape of the probe is not material so long as it minimizes the drag over it as the probe protrudes into the bulk flowing liquid in the pipeline. The probe should be sized such that significant back pressure is not introduced into the line.

The DRP comprises a chamber constructed of a porous material such as wire mesh. The pore size of the mesh can be determined empirically depending on the nature of the deposit to be evaluated and the liquid flowing through the pipeline. The deposit is often an emulsified mixture with oil and water and consequently is a viscous liquid, in which case the mesh size needs to be small enough to prevent the material naturally passing through the pores but large enough to allow the material to be removed with the action of the chemical and liquid flow. Typical mesh sizes are about 80 (i.e. 80 holes per square inch) to about 150. In 80 mesh material, for example, the hole diameter is about 0.007 inches and the wire diameter is about 0.0055 inches. The wire should be manufactured from a corrosion resistant material like stainless steel. It should be understood that the pore size can in certain instances vary considerably from the above range based on the nature of the deposit sample. For example, a larger pore size would be acceptable for mineral samples such as sand or clay.

In an embodiment, DRP comprises a substantially cylindrical chamber which is capped on both ends with an impermeable material which is inert to the fluids being transported in the pipeline. Representative impermeable materials include polyetherether ketone (PEEK) and poly tetrafluoro ethylene (PTFE), and the like.

The DRP further comprises means for supporting the probe in the pipeline. Means for supporting equipment in pipelines is known in the art. In an embodiment, the probe attaches to a standard fitting such as a Cosasco plug, which screws through a standard 2" threaded access fitting. This is inserted and subsequently removed from the pipeline using a standard coupon removal tool.

As discussed above, deposit formation in pipelines can lead to high localized corrosion rates. In an embodiment, the DRP of this invention can be used in combination with standard corrosion coupons to measure localized corrosion in the presence of deposits.

According to this embodiment, at least one standard corrosion coupon is installed in the chamber such that it is in contact with the deposit sample placed in the chamber. The coupons have the same metallurgy as the pipeline. Common metallurgies include 1018, X-52, X-65, X-70 and the like.

In another embodiment, the DRP further comprises at least one additional corrosion coupon installed on the DRP such that it is exposed to the bulk liquid flowing through the pipeline but not in contact with the deposit sample contained in the chamber. As described below, the corrosion coupons are used to determine corrosion rates for surfaces of the pipeline in contact with deposits and in contact with bulk fluids flowing through the pipeline.

Figure 2:
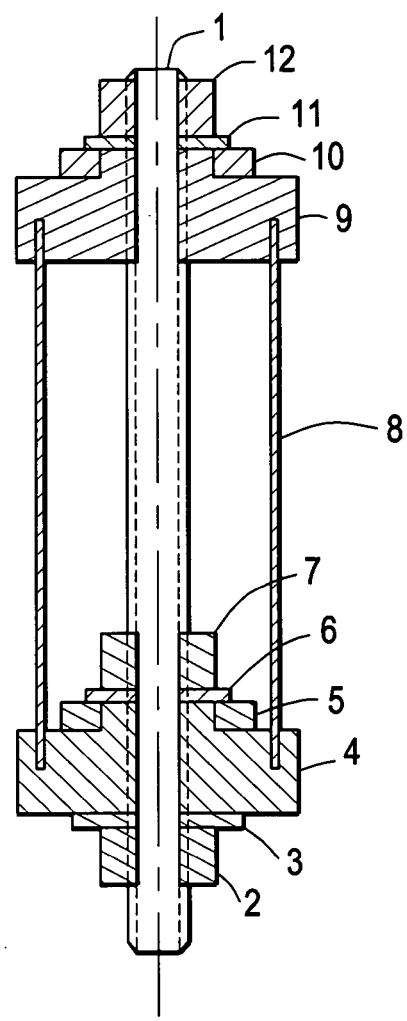
FIG. 2 is a cross-section view of a deposit removal probe according to an embodiment of this invention.

A deposit removal probe according to an embodiment of this invention is shown schematically in FIGS. 1 and 2. The probe may be constructed as described below. It is understood that the pipeline size and access fittings will dictate the actual dimensions for the probe.

A long ¼"-20 316 stainless steel rod 1 is cut to the desired length.

Top and bottom body sections 9 and 4 are constructed of PEEK material and machined on a lathe. Both sections are manufactured with a groove which supports the wire mesh 8. The top section 9 has a ¼" bore through which the threaded bolt 1 passes. The bottom section 4 contains a threaded ¼"-20 'nut' which the threaded rod 1 screws in to.

Corrosion evaluation coupons 5 and 10 are machined out of the same material as that of the pipeline that the probe will be used in, in this example C-1018.

Non-metallic washers 6 and 11 are Silicone or PTFE. Mesh 8, ¼" wide washer 3 and jam nuts 2, 7 and 12 are 316 stainless steel.

The first ¼" jam nut 2 is screwed onto the threaded rod 1 making sure that sufficient length of rod is exposed to screw into the solid plug part (weight loss coupon holder, not shown). The ¼" wide washer 3 is inserted and the threaded ¼"-20 bottom body 4 is screwed down until it sits on the ¼" wide washer 3.

The first coupon 5 is placed on the top of bottom body 4, then the ¼" non-metallic washer is placed on the coupon 5 to avoid metallic contact between coupon and other metal parts of the DRP. The second ¼"-20 jam nut 7 is screwed onto rod 1 to hold down the first coupon 5.

Wire mesh having the desired pore size is rolled into a tube, the diameter of which matches the groove in the PEEK end caps 4 and 9 to form a mesh tube 8 and the sides of the mesh tube are spot welded. The wire mesh tube 8 is placed into the groove on the bottom PEEK section 4 and the upper PEEK section 9 is then placed over the top of the wire mesh tube 8.

The second coupon 10 is placed on the top of upper PEEK section 9, then the ¼" non-metallic washer 11 placed on top of coupon 10 to insulate the coupon from the other metal parts.

The last ¼"-20 jam nut 12 is screwed onto the top of the central threaded rod 1 to hold the second coupon in place and tightened to pull the upper and lower PEEK sections 4 and 9 together.

In a typical application, the two corrosion coupons 5 and 10 are weighed. The full probe assembly is also weighed (with coupons in place). The top PEEK section 9 of the probe is removed and a representative, homogeneous sample of a deposit from the pipeline to be evaluated is placed inside the mesh tube 8. Care is taken during the filling to ensure that the lower metal coupon 5 is evenly covered with the deposit and the chamber is filled homogeneously. The mesh tube 8 is filled to the top then the upper PEEK section 9 is pushed into the top of the tube 8, squeezing any excess deposit through the sides of the mesh. Excess material is wiped from the sides of the mesh. The upper peek section 9 is fitted with the second corrosion coupon 10 and bolted in place. The fully loaded probe is then weighed again to quantify the amount of deposit charged to the probe.

The probe is then attached to a Cosasco plug and is inserted into the pipeline through a standard corrosion probe access port. The probe is left in place for a predetermined time dependent upon the anticipated effectiveness of the chemical program to be evaluated. The probe is then removed and a visual observation of the volume of deposit remaining made. Excess liquid is then drained from the probe, and then the probe assembly is weighed. The weight of deposit remaining, hence the removal efficiency is then calculated. The two coupons, one from the top of the probe, previously exposed just to the liquids in the pipeline, and the other from under the deposit in the chamber, are then removed. The coupons are cleaned and the weight loss calculated. From these values the corrosion rates in the bulk liquid, and under the deposit, are calculated.

In an embodiment, the chemical program comprises one or more deposit control chemicals.

In an embodiment, the chemical program comprises one or more corrosion inhibitors.

Changes can be made in the composition, operation and arrangement of the method of the invention described herein without departing from the concept and scope of the invention as defined in the claims.

The invention claimed is:

1. A method of monitoring the effectiveness of a chemical at removing deposits from the internal surface of a pipeline comprising
    (a) providing a probe comprising a chamber constructed from mesh having a pore size sufficient to retain a sample of said deposit in said chamber while also allowing the deposit to be removed from the chamber with the action of the chemical and liquid flow through the pipeline;
    (b) placing a weighed sample of said deposit in said chamber;
    (c) inserting said probe in said pipeline;
    (d) adding a known amount of said chemical to said fluids being transported in said pipeline;
    (e) periodically removing said probe from said pipeline and weighing said deposit sample; and
    (f) determining the amount of said sample dissolved or dispersed by said chemical.

2. The method of claim 1 wherein said fluid is crude oil, water, gas or a mixture thereof.

3. The method of claim 2 wherein said deposit is selected from organic, inorganic, mineral and microbial deposits and combinations thereof.

4. The method of claim 3 wherein said deposit is selected from heavy oil, wax, asphaltenes, sulfur, biomass, sand, clay and mineral scales and combinations thereof.

5. A method of determining the corrosion rate of an internal surface of a pipeline used to transport fluids wherein said surface is in contact with deposits in said pipeline comprising
(a) providing a probe comprising a chamber constructed from mesh having a pore size sufficient to retain a sample of said deposit in said chamber while also allowing the deposit to be removed from the chamber with the action of the chemical and liquid flow through the pipeline;
(b) placing a weighed corrosion coupon having the same metallurgy as said pipeline in said chamber;
(c) placing a weighed sample of said deposit in said chamber such that said corrosion coupon is in contact with said deposit sample;
(d) inserting said probe in said pipeline;
(e) periodically removing said probe from said pipeline and cleaning and weighing said corrosion coupon; and
(f) determining the corrosion rate of said metallurgy in contact with said deposit.

6. The method of claim 5 further comprising adding one or more corrosion inhibitors to said pipeline and determining the corrosion rate in the presence of such corrosion inhibitors.

7. The method of claim 5 further comprising adding one or more deposit-control chemicals to said pipeline and determining the corrosion rate in the presence of said deposit-control chemicals.

8. The method of claim 5 wherein said fluid is crude oil.

9. The method of claim 5 wherein said deposit is selected from organic, inorganic, mineral and microbial deposits and combinations thereof.

10. The method of claim 9 wherein said deposit is selected from heavy oil, wax, asphaltenes, sulfur, biomass, sand, clay and mineral scales and combinations thereof.

11. The method of claim 5 further comprising
(g) placing a second weighed corrosion coupon having the same metallurgy as said pipeline in said probe outside said chamber such that said second corrosion coupon is exposed to fluid in said pipeline but is not exposed to said deposit sample;
(h) periodically removing said probe from said pipeline and cleaning and weighing said corrosion coupon in contact with said deposit and said second corrosion coupon; and
(i) determining the corrosion rate of said metallurgy in contact with said deposit and not in contact with said deposit.

12. The method of claim 11 further comprising adding one or more corrosion inhibitors to said pipeline and determining the corrosion rate in the presence of such corrosion inhibitors.

13. The method of claim 11 further comprising adding one or more deposit-control chemicals to said pipeline and determining the corrosion rate in the presence of said deposit-control chemicals.

14. A deposit removal probe for monitoring the effectiveness of a chemical at removing deposits from an internal surface of a pipeline used to transport fluids comprising a chamber constructed from mesh having a pore size sufficient to retain a sample of a deposit removed from the internal surface of the pipeline upstream of the chamber via the action of chemical and liquid flow through the pipeline to enter into said chamber while also allowing the deposit to be removed from the chamber with the action of chemical and liquid flow through the pipeline.

15. The deposit removal probe according to claim 14 wherein said chamber is substantially cylindrical and capped on both ends with an impermeable material which is inert to the fluids being transported in the pipeline.

16. The deposit removal probe according to claim 14 further comprising means for supporting said probe in said pipeline.

17. The deposit removal probe according to claim 14 further comprising at least one corrosion coupon which is installed inside said chamber such that it is in contact with said sample placed in said chamber.

18. The deposit removal probe according to claim 14 further comprising at least one corrosion coupon which is installed outside said chamber and not in contact with said sample placed in said chamber.

19. A deposit removal probe for monitoring the effectiveness of a chemical at removing deposits from the internal surface of a pipeline used to transport fluids comprising a chamber constructed from mesh having a pore size sufficient to retain a sample of said deposit in said chamber while also allowing the deposit to be removed from the chamber with the action of the chemical and liquid flow through the pipeline, further comprising (i) at least one corrosion coupon which is installed inside said chamber such that it is in contact with said sample placed in said chamber and/or (ii) at least one corrosion coupon which is installed outside said chamber and not in contact with said sample placed in said chamber.

* * * * *